(12) United States Patent
Kuiper

(10) Patent No.: US 11,378,822 B2
(45) Date of Patent: Jul. 5, 2022

(54) ELECTROWETTING OPHTHALMIC DEVICES WITH ANION GETTER

(71) Applicant: Verily Life Sciences LLC, South San Francisco, CA (US)

(72) Inventor: Stein Kuiper, South San Francisco, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 325 days.

(21) Appl. No.: 16/709,186

(22) Filed: Dec. 10, 2019

(65) Prior Publication Data
US 2020/0192123 A1    Jun. 18, 2020

Related U.S. Application Data

(60) Provisional application No. 62/778,608, filed on Dec. 12, 2018.

(51) Int. Cl.
*G02C 7/08* (2006.01)
*G02B 3/14* (2006.01)
(Continued)

(52) U.S. Cl.
CPC ............ *G02C 7/085* (2013.01); *A61F 2/1613* (2013.01); *C25D 11/022* (2013.01); *G02B 3/14* (2013.01);
(Continued)

(58) Field of Classification Search
CPC ......... G02C 7/085; A61F 2/1613; G02B 3/12; G02B 3/14; G02B 26/005; G02B 2207/115
(Continued)

(56) References Cited

U.S. PATENT DOCUMENTS 8,157,797 B2    4/2012  Boukhny et al.
8,854,739 B2 *  10/2014 Kuiper .................... G02B 3/14
                                                        359/665
(Continued)

FOREIGN PATENT DOCUMENTS

DE         10024363 A1    5/2000
WO       2007107589 A1    9/2007
(Continued)

OTHER PUBLICATIONS

Langmuir 2009, 25, 20, 12387-12392; Publication Date:Aug. 13, 2009; https://doi.org/10.1021/la9016933 (Year: 2009).*
(Continued)

*Primary Examiner* — Zachary W Wilkes
(74) *Attorney, Agent, or Firm* — Christensen O'Connor Johnson Kindness PLLC

(57) ABSTRACT

An ophthalmic device includes an enclosure, two immiscible fluids, an electrode, a dielectric, and an anion getter material. The enclosure is configured to mount on or in an eye of a user. The two immiscible fluids, including a first fluid and a second fluid, are disposed within the enclosure. The electrode is separated from the two immiscible fluids by the dielectric. The electrode is capable of forming a barrier layer during an anodization process when a voltage is applied across the electrode and the first fluid. The anion getter material is disposed within the ophthalmic device and is capable of gettering anion contaminants that inhibit the anodization process from forming the barrier layer.

23 Claims, 7 Drawing Sheets

(51) Int. Cl.
*G02B 26/00* (2006.01)
*C25D 11/02* (2006.01)
*A61F 2/16* (2006.01)

(52) U.S. Cl.
CPC ...... *G02B 26/005* (2013.01); *G02B 2207/115* (2013.01)

(58) Field of Classification Search
USPC ........................................ 351/159.34, 159.68
See application file for complete search history.

(56) References Cited

U.S. PATENT DOCUMENTS

| | | | |
|---|---|---|---|
| 9,244,203 B2 * | 1/2016 | Otts | .......................... G02B 3/12 |
| 9,414,908 B2 | 8/2016 | Maillard | |
| 10,175,470 B2 * | 1/2019 | Malone | ............. H02M 3/33507 |
| 10,509,238 B2 * | 12/2019 | Otts | ........................ G02C 7/083 |
| 2004/0150788 A1 | 8/2004 | Andersson et al. | |
| 2014/0350554 A1 | 11/2014 | Keller | |
| 2016/0259094 A1 | 9/2016 | Aschwanden et al. | |
| 2018/0116207 A1 | 5/2018 | Mahadevan et al. | |
| 2018/0217370 A1 * | 8/2018 | Malone | ............. H02M 3/33507 |
| 2019/0079317 A1 * | 3/2019 | Kuiper | .................... G02C 11/10 |
| 2020/0298238 A1 * | 9/2020 | Kim | .................. B01L 3/502792 |

FOREIGN PATENT DOCUMENTS

| | | |
|---|---|---|
| WO | 2018182852 A1 | 10/2018 |
| WO | 2019051311 A1 | 3/2019 |

OTHER PUBLICATIONS

Mini-Donut Catches Chloride Ions, Phys.Org, Mar. 11, 2008, 2 pages.
Amar Flood Research Group, http://www.indiana.edu/~floodweb, May 1, 2018, 7 pages.
Schuliz et al., "Detailed analysis of defect reduction in electrowetting dielectrics through a two-layer 'barrier' approach", Thin Solid Films, www.elsevier.com/locate/tsf, Aug. 27, 2012, 9 pages.
Dhindsa et al, "Electrowetting without Electrolysis on Self-Healing Dielectrics", American Chemical Society, Langmuirpubs.asc.org/Langmuir, Dec. 31, 2010, 6 pages.
Panitz et al., "The Use of Synthetic Hydrocalcite as a Chloride-Ion Getter for a Barrier Aluminum Anodization Process", Nov. 1, 1995, www.osti.gov/servlets/purl/176817, 30 pages.
Dhindsa et al., "Electrowetting without Electrolysis on Self-Healing Dielectrics", Langmuir, vol. 27, No. 9, May 3, 2011, 8 pages.
International Search Report and Written Opinion, dated Apr. 6, 2020, for corresponding International Patent Application No. PCT/US2019/065786, 28 pages.
Khodayari et al., "A Material System for Reliable Low Voltage Anodic Electrowetting", Mechanical Engineering Department, University of South Florida, arXiv:1302.6308 [cond-mat.mtrl-sci], Feb. 2013, pp. 1-10.
Choi, Jinsub, "Fabrication of Monodomain Porous Alumina Using Nanoimprint Lithograph and Its Applications", Universitats- und Landesbibliothek Sachsen-Anhalt, 2004, Retrieved from the Internet: <URL:https://sundoc.bibliothek.uni-halle.de/diss-online/04/04FI055/t2.pdf> Chapter 1, pp. 1-12.

* cited by examiner

ELECTROWETTING OPHTHALMIC DEVICES WITH ANION GETTER

CROSS-REFERENCE TO RELATED APPLICATIONS

This application claims the benefit of U.S. Provisional Application No. 62/778,608, filed Dec. 12, 2018, which is hereby incorporated by reference in its entirety.

TECHNICAL FIELD

This disclosure relates generally to the field of ophthalmic devices, and in particular but not exclusively, relates to electrowetting ophthalmic devices.

BACKGROUND INFORMATION

Contact lenses are worn by a large number of people throughout the world, mainly for the purpose of vision correction. However, as lens technology continues to progress, the functionality of contact lenses may extend beyond merely providing static vision correction to other areas. For example, eye-mountable devices (EMD), smart contact lenses, or intraocular lenses may offer unique opportunities in health monitoring, biometric sensing, dynamic vision correction, and other types of vision augmentation.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Embodiments of electrowetting ophthalmic devices with an anion getter material are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Ophthalmic devices, such as eye-mountable devices, contact lenses, intraocular lenses, and the like, may have various functionalities, such as, but not limited to, providing assistance in accommodation when a user's lens is no longer able to change focus as desired, as is the case for most individuals over the age of forty who are afflicted by presbyopia in varying degrees. The ophthalmic device may have a lens which provides static optical power or may have the ability to dynamically accommodate (e.g., alter the optical power of the ophthalmic device provided by the lens), so that the user may change focus similar to the natural eye.

The lifetime of ophthalmic devices is closely tied to the device architecture, material composition, fabrication techniques, operational characteristics, and so on. It may be desirable for intraocular lenses, for example, to have a lifetime spanning ten or more years due to the invasive nature of replacing a device that is implanted within an eye of a user. Another important aspect of ophthalmic devices is safe and reliable operation, which is intrinsically tied to the lifetime of the device. Described herein are embodiments of ophthalmic devices which utilize a self-healing system including an anion getter material to inhibit detrimental effects of anion contaminants which may diffuse into the ophthalmic device over the course of its lifetime.

Figure 1:
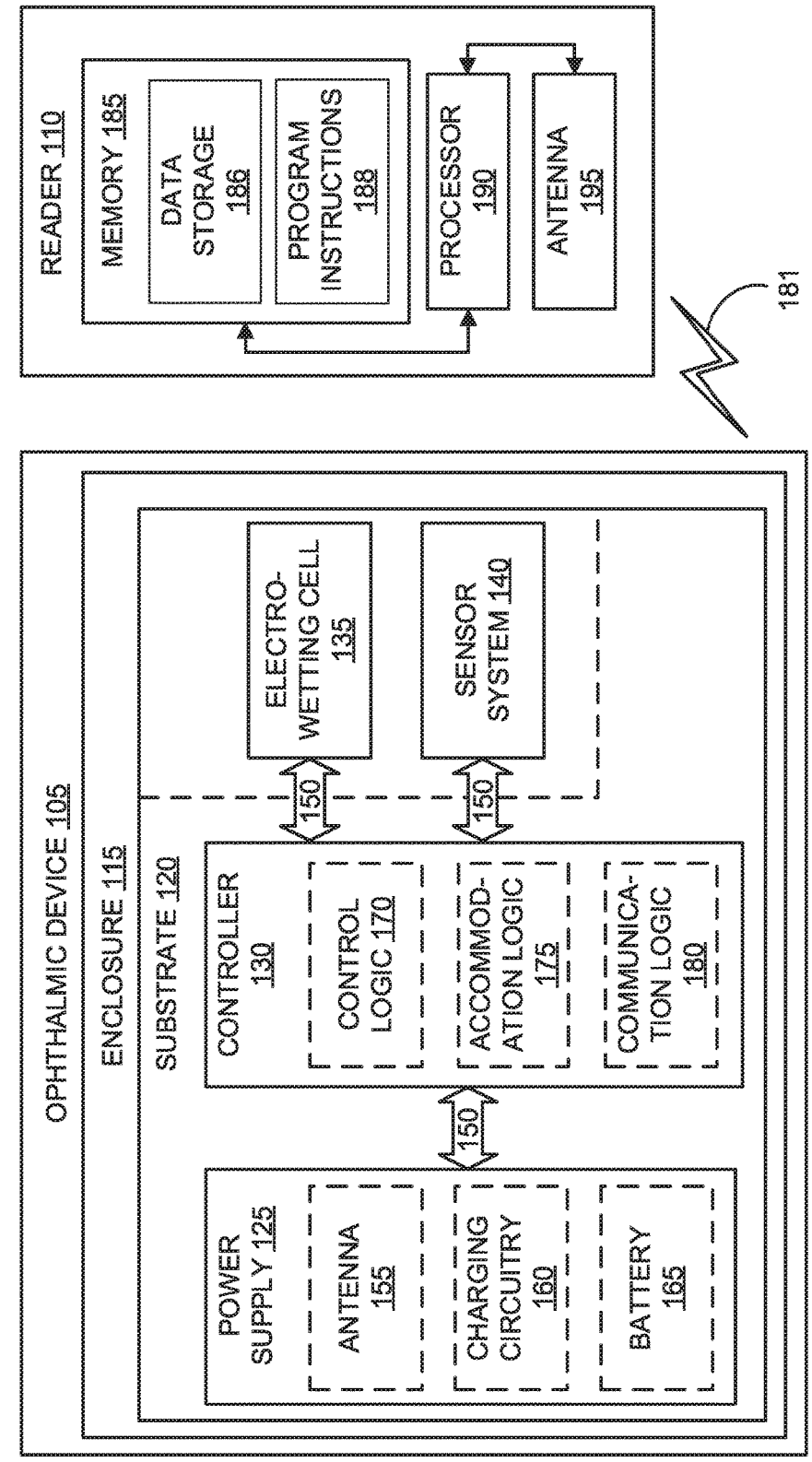
FIG. 1 illustrates a functional block diagram of an electrowetting ophthalmic device along with an external reader, in accordance with an embodiment of the disclosure.

FIG. 1 illustrates a functional block diagram 100 of an electrowetting ophthalmic device 105 along with an external reader 110, in accordance with an embodiment of the disclosure. The exposed portions of ophthalmic device 105 includes an enclosure 115 configured to be contact-mounted to a corneal surface, sclera, or other portion of an eye of a user. Alternatively, ophthalmic device 105 may be disposed within the eye of the user (e.g. within the capsular sac of the eye). Substrate 120 is embedded within or surrounded by enclosure 115 and may provide a mounting surface for power supply 125, controller 130, electrowetting cell 135, sensor system 140, and various interconnects 150. Alternatively, enclosure 115 may provide a mounting surface for the various components of the ophthalmic device 105 in lieu of, or in addition to, substrate 120. The illustrated embodiment of power supply 120 includes an antenna 155, charging circuitry 160, and a battery 165. As illustrated, controller 130 includes control logic 170, accommodation logic 175, and communication logic 180. The illustrated embodiment of reader 110 includes memory 185, a processor 190, and an antenna 195. The illustrated embodiment of memory 186 includes data storage 188 and program instructions 190.

Controller 130 is coupled to receive feedback control signals from sensor system 140 and further coupled to operate electrowetting cell 135. Power supply 125 supplies operating voltages to controller 130, electrowetting cell 135, and/or sensor system 140. Antenna 155 is operated by controller 130 to communicate information to and/or from ophthalmic device 105 (e.g., transmit data, information, commands, and the like between ophthalmic device 105 and external reader 110). In the same or other embodiments, antenna 155 in conjunction with charging circuitry 160 may be operable to wirelessly charge battery 165 (e.g., via RF wireless charging, induction charging, and the like). In one embodiment, power supply 125, controller 130, electrowetting cell 135, and sensor system 140 are all situated on substrate 120. In other embodiments, electrowetting cell 135 is embedded within enclosure 115, but not disposed on substrate 120. Because ophthalmic device 105 includes electronics and is configured to be contact-mounted to or disposed within an eye, it is also referred herein as an ophthalmic electronics platform, eye-mountable device, contact lens, smart contact lens, or intraocular lens.

Enclosure 115 may include one or more biocompatible materials, such as those employed for use in contact lenses, intraocular lenses, or other ophthalmic applications. Enclosure 115 may optionally be formed in part from such biocompatible materials or may include an outer coating with such biocompatible materials. Enclosure 115 may include materials configured to moisturize the corneal surface, such as hydrogels (e.g., silicone hydrogel), and the like. In some embodiments, enclosure 115 may be composed of one or more materials such that enclosure 115 is a deformable, foldable, or otherwise "non-rigid" structure to enhance wearer comfort. In the same or other embodiments, enclosure 115 may be shaped such that ophthalmic device 105 provides a predetermined, vision-correcting (or otherwise) optical power. Enclosure 115 may be fabricated of various materials including a polymeric material, polyethylene terephthalate ("PET"), polymethyl methacrylate ("PMMA"), polyhydroxyethylmethacrylate ("polyHEMA"), a hydrogel, silicone, silicone based polymers (e.g., fluoro-silicone acrylates), AcrySof® proprietary co-polymers, other co-polymers, parylene, combinations of these, or otherwise.

Substrate 120 includes one or more surfaces suitable for mounting power supply 125, controller 130, electrowetting cell 135, and sensor system 140. Substrate 120 may be employed both as a mounting platform for chip-based circuitry (e.g., by flip-chip mounting) and/or as a platform for patterning conductive materials (e.g. gold, platinum, palladium, titanium, copper, aluminum, silver, nanowires, valve metals, other metals, other conductive materials, combinations of these, etc.) to create electrodes, interconnects, antenna(s), etc. In some embodiments, substantially transparent conductive materials (e.g., indium tin oxide, metal nanowire mesh, and the like) may be patterned on substrate 120 or otherwise disposed within enclosure 115 for circuitry, electrodes, etc. In the same or other embodiments, conductive materials may comprise a valve metal (e.g., aluminum, hafnium, niobium, tantalum, titanium, tungsten, vanadium, zirconium, bismuth) as part of a self-healing system. In one embodiment, antenna 155 may be formed by depositing a pattern of gold or another conductive material on substrate 120. Similarly, interconnects 150 may be formed by depositing suitable patterns of conductive materials on the substrate 120, or otherwise within enclosure 115. A combination of resists, masks, and deposition techniques may be employed to pattern materials on substrate 120. Substrate 120 may be a relatively rigid material, such as polyethylene terephthalate ("PET"), Parylene C, Parylene HT, polyimide, another material, or a combination of materials sufficient to structurally support the circuitry and/or electronics within enclosure 115. In other embodiments, ophthalmic device 105 may alternatively be arranged with a group of physically distinct substrates rather than a single substrate. In one embodiment, controller 130, battery 165, and electrowetting cell 135 may be mounted to one substrate, while antenna 155 and sensor system 140 are mounted to another substrate and the two substrates may be electrically connected or otherwise coupled via interconnects 150.

In some embodiments, power supply 125, controller 130, and sensing system 140 may be positioned away from the center (e.g., within a peripheral region) of ophthalmic device 105 and thereby avoid interference with light transmission to the eye through the center of ophthalmic device 105. In contrast, electrowetting cell 135 may be centrally positioned to provide accommodation for the wearer of ophthalmic device 105 by correcting the light (e.g., applying or adjusting optical power applied) transmitted to the eye through the center of ophthalmic device 105. In some embodiments, sensor system 140 includes a sensor trace electrically coupled to one or more discrete photodetectors (e.g., photodiodes), capacitors, electrochemical sensors, electrodes/traces, and the like, that are distributed, for example, to sense eyelid overlap, gaze direction, analyte levels, and the like. In some embodiments, sensor system 140 and/or substrate 120 are substantially transparent to incoming visible light to mitigate interference with light transmission to the eye.

In the illustrated embodiment, power supply 125 includes a battery 165 to power the various embedded electronics, including controller 130, electrowetting cell 135, and sensor system 140. Battery 165 may be inductively charged by charging circuitry 160 and antenna 155 acting as an energy harvesting antenna. In some embodiments, battery 165 may be a capacitor. In the illustrated embodiment, antenna 155 is time-shared for inductive charging and wireless communications with reader 110. In other embodiments, separate antennas may be utilized to individually and simultaneously provide the respective functions of inductive charging and wireless communication.

Charging circuitry 160 may include a rectifier/regulator to condition the captured energy for charging battery 165 or directly powering controller 130 without battery 165. Charging circuitry 160 may also include one or more energy storage devices to mitigate high frequency variations that may be present when antenna 155 is used for inductive or RF wireless charging. In one embodiment, charging circuitry 160 includes one or more energy storage devices (e.g., a capacitor, an inductor, etc.) coupled to function as a low-pass filter.

Controller 130 contains logic to choreograph the operation of the other embedded components of ophthalmic device 105. Control logic 170 controls the general operation of ophthalmic device 105, including providing a logical user interface, power control functionality, accommodation adjustment, etc. Accommodation logic 175 includes logic for monitoring feedback signals from sensor system 140, determining the current gaze direction or focal distance of the user, and manipulating electrowetting cell 135 in response to the feedback signals to provide the appropriate accommodation to the user. In some embodiments, auto-accommodation may be implemented in real-time based upon feedback from the gaze tracking (e.g., via sensor system 140), or permit the user control to select specific accommodation regimes (e.g., near-field accommodation for reading, far-field accommodation for regular activities, and the like). Communication logic 180 provides communication protocols for wireless communication with reader 110 via antenna 155. In one embodiment, communication logic 180 provides backscatter communication via antenna 155 when in the presence of an electromagnetic field 181 output from reader 110. In one embodiment, communication logic 180 operates as a smart wireless radio-frequency identification ("RFID") tag that modulates the impedance of antenna 155 for backscatter wireless communications. The various logic modules of controller 130 may be implemented in software/firmware (e.g., controller 130 may include a processor coupled to memory storing instructions), in hardware logic (e.g., application specific integrated circuits, field-programmable gate arrays, and so on), or a combination of both that when executed causes ophthalmic device 105 to perform operations (e.g., adjusting a shape of a lens included in electrowetting cell 135 to provide auto-accommodation based on feedback signals from sensor system 140).

It is noted that the block diagram shown in FIG. 1 is described in connection with functional modules for convenience in description, but does not necessarily connote physical organization. Rather, embodiments of ophthalmic device 105 may be arranged with one or more functional modules ("sub-systems") implemented in a single chip, multiple chips, in one or more integrated circuits, or otherwise.

External reader 110 includes an antenna 195 (or group of more than one antennas) to send and receive wireless signals 181 to and from ophthalmic device 105. External reader 110 also includes a computing system with a processor 190 in communication with memory 186. Memory 186 is a non-transitory computer-readable medium that may include, without limitation, magnetic disks, optical disks, organic memory, and/or any other volatile (e.g., RAM) or non-volatile (e.g., ROM) storage system readable by processor 190. Memory 185 may include data storage 186 to store indications of data, such as data logs and program settings (e.g., to adjust behavior of ophthalmic device 105 and/or external reader 110), etc. Memory 185 may also include program instructions 188 for execution by processor 190 to cause external reader 110 to perform processes specified by the program instructions 188. In some embodiments, external reader 110 may be a smart phone or other portable computing device capable of wirelessly communicating with ophthalmic device 105.

Figure 2A:
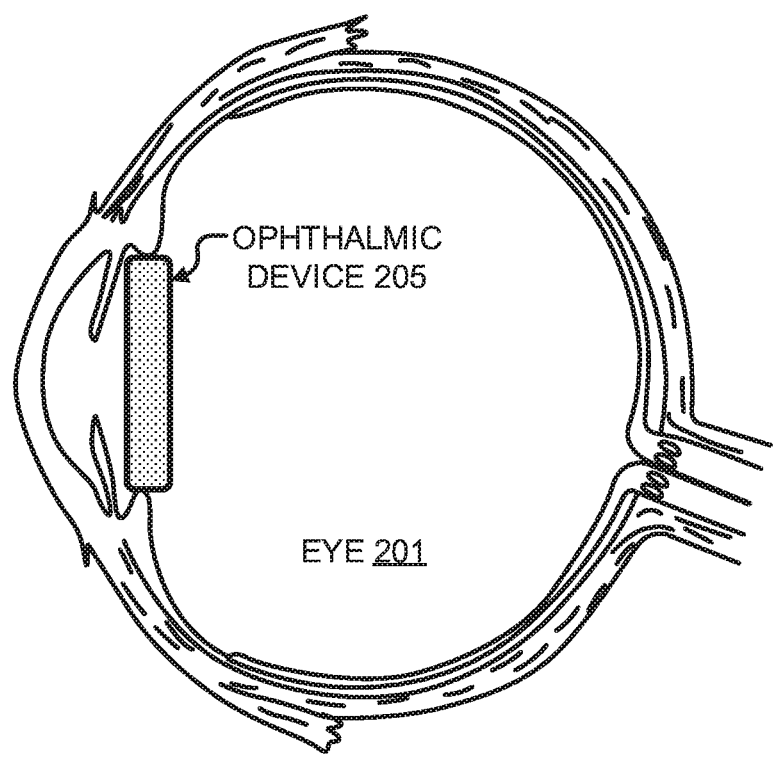
FIG. 2A illustrates a side view of an ophthalmic device mounted on an eye, in accordance with an embodiment of the disclosure.
Figure 2B:
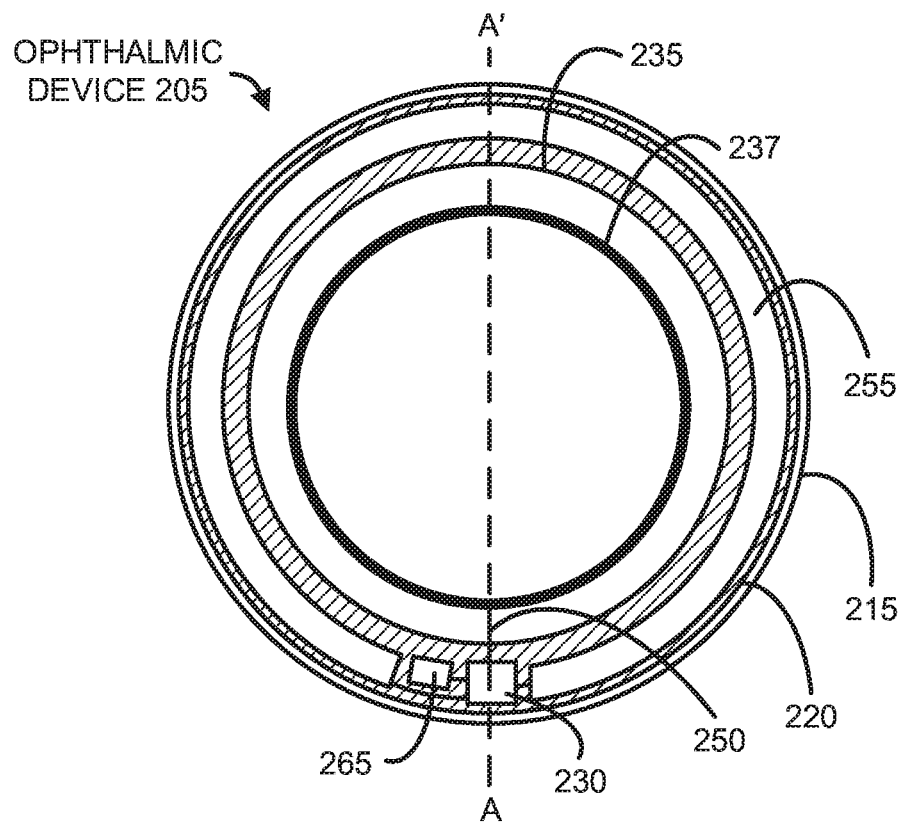
FIG. 2B illustrates a top view of an ophthalmic device, in accordance with an embodiment of the disclosure.

FIGS. 2A and 2B illustrate two views of ophthalmic device 205, in accordance with an embodiment of the disclosure. FIG. 2A is a side view of ophthalmic device 205 implanted within the capsular sac of eye 201, while FIG. 2B is a top view of ophthalmic device 205. Ophthalmic device 205 includes enclosure 215, substrate 220, controller 230, electrowetting cell 235, electrode 237, interconnect 250, antenna 255, and battery 265, which may be analogous to their identically named components included in ophthalmic device 105 of FIG. 1. In other words, ophthalmic device 205 is one possible implementation of ophthalmic device 105 illustrated in FIG. 1, and may include the same or similar features, structures, characteristics, or combination thereof in accordance with embodiments of the present disclosure.

As illustrated in FIG. 2A, ophthalmic device 205 is an intraocular device configured to be mounted in an eye. More specifically, the illustrated embodiment shows ophthalmic device 205 implanted where the natural eye lens would typically be located proximate to the ciliary muscle. In one embodiment, ophthalmic device 205 may include a sensor system (e.g., sensor system 140 illustrated in FIG. 1) to sense an accommodative effort (e.g., indicated by the ciliary muscle) to determine a level of accommodation to provide with ophthalmic device 205. It is further appreciated that in other embodiments ophthalmic device 205 may be implanted within the posterior chamber behind an iris of eye 201, the anterior chamber disposed between the iris and cornea, as well as other locations.

In some embodiments, ophthalmic device 205 is capable of being rolled up into a cylindrical shape or folded, such that a smaller incision may be utilized to insert or otherwise implant ophthalmic device 205 within the eye relative to a larger incision necessary for implantation of the ophthalmic device 205 in an unfolded or unrolled state. Thus, in general, ophthalmic device 205 is a flexible device that may comprise materials that are amenable to being rolled, folded, or otherwise elastically deformed. However, the stresses applied to ophthalmic device 205 during deformation may inadvertently damage or reduce the lifetime of the device. Moreover, material degradation and dielectric fatigue may cause shorts in the dielectric layer inside the device. To mitigate these effects, ophthalmic device 205 uses a self-healing system that relies on forming a barrier oxide. However, over time contaminants (e.g., anion contaminants such as chloride) present within the eye may diffuse into ophthalmic device 205 and interfere with the oxide formation. To mitigate these effects, ophthalmic device 205 utilizes a self-healing system that includes one or more anion getter materials that may inhibit the degradation of the self-healing effect caused by contaminants.

As illustrated in FIG. 2B, ophthalmic device 205 includes substrate 220, controller 230, electrowetting cell 235, electrode 237, interconnect 250, antenna 255, and battery 265 disposed within enclosure 215. Electrowetting cell 235 is centrally located within enclosure 215 and is coupled to controller 230 via interconnect 250 to provide accommodation to the user. More specifically, electrowetting cell 235 provides optical power that is adjustable based, at least in part, on an applied potential difference (e.g., a voltage) across and/or between electrode 237 and a second electrode (not illustrated). In the illustrated embodiment, electrode 237 is a conical electrode that extends around electrowetting cell 235. In other words, electrode 237 may form a loop, circle, oval, or otherwise define a boundary within electrowetting cell 235. The inner region formed by electrode 237 (e.g., the area encircled or otherwise enclosed by electrode 237) may correspond to a central region of ophthalmic device 205, while the outer region (e.g., the area outside of the central region) may correspond to a peripheral region of ophthalmic device 205.

In the illustrated embodiment of FIG. 2B, substrate 220 may be a support structure for mounting controller 230, electrowetting cell 235, interconnect 250, antenna 255, and battery 265 within enclosure 215. In some embodiments, substrate 220 is an optically transparent (e.g., substantially transparent or otherwise transmissive to light within the visible spectrum of electromagnetic radiation) substrate formed from transparent polymers such as cross-linked siloxanes (e.g., polydimethylsiloxanes), transparent polyetherimide resins such as ULTEM™ manufactured by SABIC, PET, methylmethacrylates, and the like. In one embodiment, substrate 220 may be a support structure for the various components (e.g., electrode 237) of electrowetting cell 235. In another embodiment, substrate 220 is an annular substrate coupled to the electrowetting cell 235, which includes a support structure or substrate that is separate from the annular substrate.

Figure 3A:
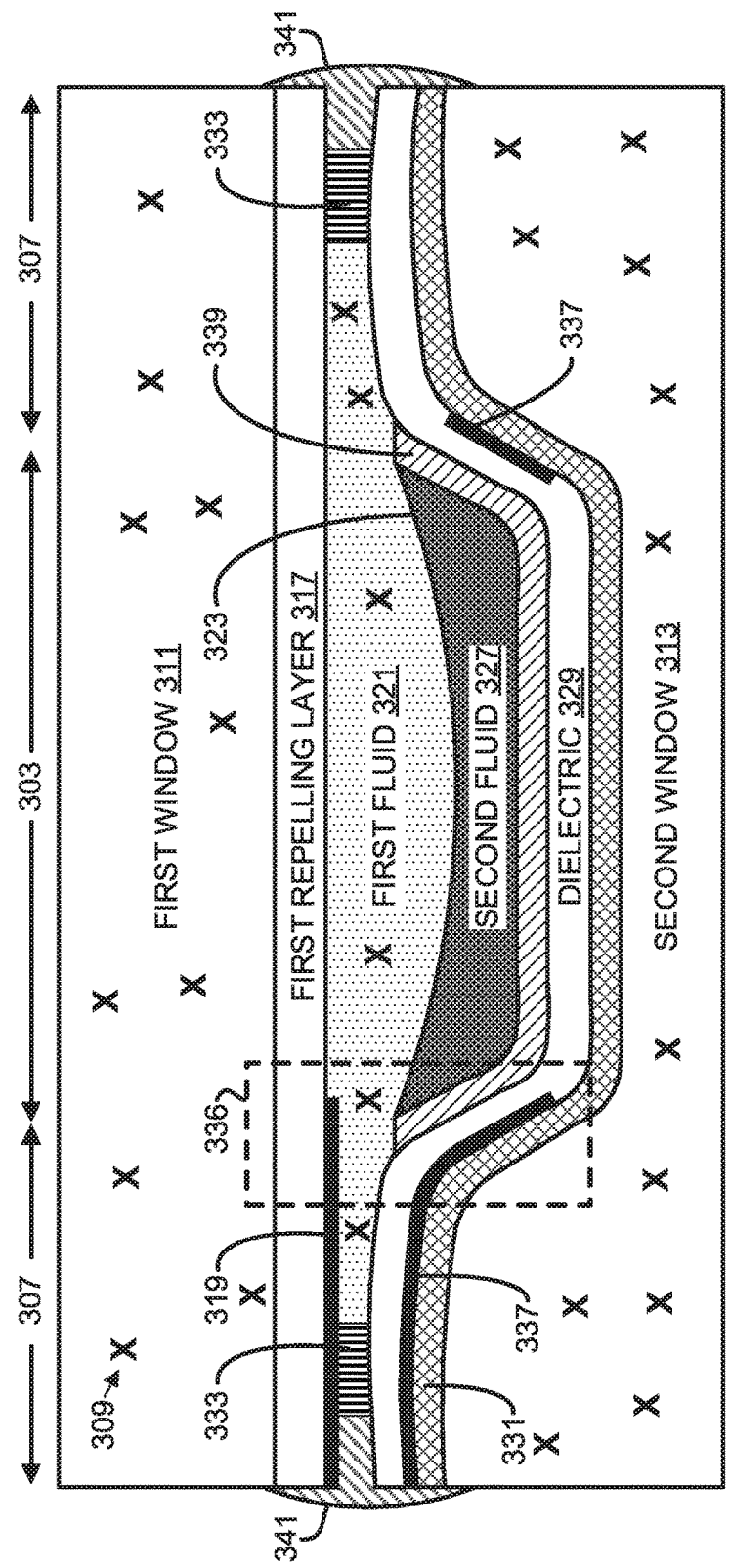
FIG. 3A illustrates a cross-sectional view of an electrowetting cell of an ophthalmic device with an anion getter material disposed within the ophthalmic device, in accordance with an embodiment of the disclosure.

FIG. 3A illustrates a cross-sectional view of an electrowetting cell 335 included in an ophthalmic device (e.g., ophthalmic device 105 of FIG. 1 and/or ophthalmic device 205 of FIG. 2A) with an anion getter material disposed within the ophthalmic device, in accordance with an embodiment of the disclosure. Electrowetting cell 335 is one possible implementation of electrowetting cell 135 of FIG. 1 and/or electrowetting cell 235 of FIG. 2B. Thus, electrowetting cell 335 may be included in ophthalmic device 105 of FIG. 1 and/or ophthalmic device 205 of FIG. 2A. In some embodiments, electrowetting cell 335 itself is a wholly contained ophthalmic device, with certain features (e.g., a controller, power supply, sensor system, etc.) analogous to those described in embodiments of the disclosure (e.g., ophthalmic 105 of FIG. 1) omitted to avoid obscuring certain aspects of the disclosure. In one embodiment, electrowetting cell 335 is representative of a cross-sectional view of ophthalmic device 205 of FIG. 2B along line A-A' with controller 230 and antenna 255 omitted.

In the illustrated embodiment of FIG. 3A, electrowetting cell 335 includes anion getter material 309, first window 311, second window 313, first repelling layer 317, second repelling layer 339, first fluid 321, second fluid 327, interface 323, dielectric 329, electrode 319, electrode 337, support structure 331, first sealant 333, and second sealant 341. As part of an ophthalmic device, electrowetting cell 335 may be positioned in or on an eye. More specifically, in some embodiments, a central region 303 of electrowetting cell 335 is aligned with the eye to provide accommodation for the eye (e.g., within the optical path of light entering the eye), while a peripheral region 307 of the electrowetting cell 334 is positioned outside of the optical path such that the elements within the peripheral region 307 do not interfere with the vision of the user.

As illustrated in FIG. 3A, electrowetting cell 335 includes two immiscible fluids, including first fluid 321 and second fluid 327, which form an interface 323 (e.g., a meniscus). Interface 323 represents a boundary between two materials (e.g., the first fluid 321 and the second fluid 327) having different refractive indexes, which form a lens that may impart optical power on light propagating through the central region 303. In one embodiment, first fluid 321 is a polar liquid (e.g., water, glycol, etc.) while second fluid 327 is a non-polar liquid (e.g., oil such as silicone oil or alkanes). In the same or other embodiments, first fluid 321 is an electrolyte solution that is electrically conductive. For example, first fluid 321 may include a solvent (e.g., water) in which an electrolyte (e.g., citric acid) is dissolved. The electrolyte may be a chemical compound, such as a salt, an acid, or a base that dissociates into ions when dissolved in the solvent, making first fluid 321 an ionic electrical conductor. In one embodiment, first fluid 321 is a 0.01 M aqueous solution of citric acid. In another embodiment, first fluid 321 is 0.01 M ammonium citrate tribasic.

In the illustrated embodiment, the two immiscible fluids (e.g., first fluid 321 and second fluid 327) are disposed between first window 311 and second window 313. More specifically, first window 311 and second window 313 are optically transparent windows formed from one or more optically transparent materials (e.g., silicone, AcrySof® co-polymers, and the like) that in conjunction with one or more sealants (e.g., first sealant 333 and second sealant 341) enclose or otherwise encapsulate first fluid 321 and second fluid 327 within the electrowetting cell 335. Thus, in some embodiments, first window 311, second window 313, first sealant 333, second sealant 341, and/or a combination thereof corresponds to an enclosure (e.g., enclosure 115 of FIG. 1 and/or enclosure 215 of FIG. 2B) configured to mount on or in an eye. In one embodiment, first sealant 333 is a pressure sensitive adhesive (e.g., silicone pressure sensitive adhesive) and second sealant 341 is a glue (e.g., curable silicones such as two-part Pt cure silicones, RTV moisture-cure silicones, UV-curable silicones, and the like). In some embodiments, second sealant 341 is preferably elastomeric to enable folding (e.g., of the electrowetting cell 335 and/or other ophthalmic devices, in accordance with embodiments of the disclosure).

As illustrated in FIG. 3A, first fluid 321 is disposed between first window 311 and second fluid 327, while second fluid 327 is disposed between first fluid 321 and second window 313. More specifically, second fluid 327 is disposed between first fluid 321 dielectric 329. Dielectric 329 is an insulating material (e.g., a parylene based dielectric such as at least one of Parylene-C, Parylene-N, Parylene-D, and/or Parylene AF4) that prevents a short from forming between electrode 337 and electrode 319. In some embodiments dielectric 329 includes second repelling layer 339. In other words, reference to dielectric 329 may refer to a stack of a dielectric material (e.g., a parylene based dielectric) that has surface coated with a repelling layer (e.g., second repelling layer 339).

The particular orientation of first fluid 321 and second fluid 327 is attributed, at least in part, due to first repelling layer 317 and second repelling layer 339, which are selected to prevent displacing the orientation of first fluid 321 and second fluid 327 (e.g. makes it energetically unfavorable for first fluid 321 and second fluid 327 to switch positions within electrowetting cell 335). In one embodiment, first repelling layer 317 is selected to repel second fluid 327 (e.g., first repelling layer 317 is underwater oleophobic in embodiments where first fluid 321 comprises an aqueous solution and second fluid 327 comprises oil). Similarly, second repelling layer 339 is selected to repel first fluid 321 (e.g., second repelling layer 339 is hydrophobic in embodiments where first fluid 327 is an aqueous solution). In one embodiment, the first repelling layer 317 is an oil repelling layer comprising polyethylene glycol, while the second repelling layer 339 is a water repelling layer comprising a fluoropolymer such as Teflon® AF-1600 or Cytop. In some embodiments, second repelling layer 339 is omitted and a material composition of dielectric 329 provides the repelling feature in place of second repelling layer 339 (e.g., in one embodiment dielectric 329 comprises Teflon® AF-1600 while electrode 337 is a valve metal with a self-healing barrier oxide). In such an embodiment, the self-healing barrier oxide of electrode 337 compensates for the porosity of dielectric 329. It is appreciated that the examples provided of oleophobic and hydrophobic materials should not be deemed limiting and that other oleophobic and hydrophobic materials may be utilized to respectively form first repelling layer 317 and second repelling layer 339. In some embodiments, first repelling layer 317 and/or second repelling layer 339 may comprise a self-assembled monolayer to achieve the desired oleophobic or hydrophobic functionality. For example, dielectric 329 may be a metal oxide dielectric such as aluminum oxide or silicon oxide that has an inner surface (e.g., the surface between dielectric 329 and the immiscible fluid composition of first fluid 321 and second fluid 327) functionalized by long-chained alkyl silanes or phosphonic acids (e.g., octadecylphosphonic acid, octadecylsilane, and the like).

Electrowetting cell 335 also includes support structure 331 which may provide a rigid or semi-rigid backbone for the individual components of electrowetting cell 335. For example, a shape of second window 313, dielectric 329, electrode 337, and second repelling layer 339 may be based, at least in part, on an underlying shape of support structure 331. As illustrated in FIG. 3A, a cross-section of support structure 331 forms a substantially trapezoidal channel that is substantially replicated by second window 313, dielectric 329, second repelling layer 339, and electrode 337, and second window 313. In some embodiments, support structure 331 has an indentation that is circular, ovoidal, oblong, or otherwise. Edges of the indentation may be tapered (e.g., fall and/or rise at one or more predetermined angles, such as thirty degrees, forty-five degrees, or otherwise). In the same or other embodiments, support structure 331 may be an optically transparent substrate formed from transparent polymers such as polydimethylsiloxanes, cross linked siloxanes, transparent polyetherimide resins such as ULTEM™ manufactured by SABIC, and the like. In general support structure 331 is a non-elastomeric structure that mitigates electrode cracking/degradation and provides rigidity to elastomeric components (e.g., second window 313). In some embodiments, support structure 331 corresponds to (or otherwise incorporates the same features as) substrate 120 of ophthalmic device 105 illustrated in FIG. 1 and/or substrate 220 of ophthalmic device 205 illustrated in FIG. 2B.

In the illustrated embodiment of FIG. 3A, electrode 319 is disposed between first fluid 321 and first repelling layer 317, while electrode 337 is separated from the two immiscible fluids (e.g., first fluid 321 and second fluid 327) by dielectric 329. As illustrated, electrode 337 has a conical, circular, or ovoidal shape within electrowetting cell 335 (e.g., similar to electrode 237 illustrated in FIG. 2B). In some embodiments, a boundary defined by the shape of electrode 337 may define central region 303 and peripheral region 307 of electrowetting cell 335. In the illustrated embodiment, the conical portion of the electrode 337 resides on or is otherwise proximate to the tapered edges of the indentation of support structure 331. Thus, the conical portion of electrode 337 may reside at a pre-determined angle (e.g., thirty degrees, forty-five degrees, or otherwise) relative to the first window 311 or a horizontal axis of FIG. 3A, for example. More specifically, in the illustrated cross-section, a portion of the electrode 337 extends from the loop or conical portion towards an edge or side of electrowetting cell 335 (e.g., to be coupled with a controller and/or a battery as illustrated in FIG. 2B). Electrode 319 may similarly extend from an edge or side of the electrowetting cell (e.g., to also be coupled with a controller and/or a battery as illustrated in FIG. 2B). In some embodiments, electrodes 319 and 337 may comprise a valve metal (e.g., at least one of aluminum, hafnium, niobium, tantalum, titanium, tungsten, vanadium, and/or zirconium). In the same or other embodiments, electrodes 319 and 337 may also include a metal oxide grown or otherwise deposited (e.g., via anodization, sputtering, evaporation, chemical vapor deposition, and the like) on the valve metal such that the metal oxide is disposed between the valve metal and dielectric 329 (e.g., in an embodiment where electrode 337 is aluminum, the metal oxide may corresponds to aluminum oxide). In one embodiment, electrode 319 is a noble metal such as gold, silver, and/or platinum, while electrode 337 is a valve metal. In another embodiment, electrode 319 is made of the same valve metal as electrode 337.

As illustrated in FIG. 3A, electrowetting cell 335 includes one or more anion getter materials 309 (represented by the 'X' symbols in the illustrated embodiment) disposed within any of the various components of electrowetting cell 335 (e.g., within first window 311, first fluid 321, and/or second window 313 as shown in the illustrated embodiment) and capable of gettering anion contaminants that may negatively impact the device. Anion contaminants may correspond to halide anions (e.g., chloride ions, fluoride ions, and the like) as well as other anions such as phosphate ions, sulfate ions, and/or selenate ions. The anion getter material 309 getters (e.g., binds, interacts, or otherwise immobilizes or removes via a chemical reaction, electrostatic interaction, and the like) anion contaminants to inhibit their negative impact on electrowetting cell 335.

In the illustrated embodiment, anion getter material 309 is disposed within first window 311, first fluid 321, and second window 313. However, it is appreciated that in other embodiments, anion getter material 309 may not necessarily be disposed in each of first window 311, first fluid 321, and second window 313. Rather, in one embodiment anion getter material 309 is disposed in first fluid 321, but is not disposed within first window 311 or second window 313. In another embodiment, anion getter material 309 is stored within first window 311 and/or second window 313 but not within first fluid 321. In the same or other embodiments, anion getter material 309 may be disposed within other components such as first repelling layer 317, second fluid 327, second repelling layer 339, dielectric 329, first sealant 333, second sealant 341, or otherwise. In the various embodiments, anion getter material 309 may be selected, processed, or otherwise integrated into the various components of electrowetting cell 335 such that anion getter material 309 does not substantially interfere with the function of a particular component (e.g., anion getter material 309 does not substantially interfere with the electrowetting effect of electrowetting cell 335 when anion getter material 309 is disposed within the first fluid 321).

In the various embodiments, anion getter material 309 may be disposed within electrowetting cell 335 in solid or liquid form. In one embodiment, anion getter material 309 corresponds to a solute that is dissolved within first fluid 321 and/or second fluid 321 (e.g., one or more components of first fluid 321 and/or second fluid 321 correspond as a solvent of anion getter material 309). In one embodiment, anion getter material 309 may form a homogenous mixture with the solvent. In other embodiments, anion getter material 309 may from a heterogeneous mixture in the form of colloids, suspensions, and/or emulsions of anion getter material 309. The solvent may have a pre-determined solubility limit with respect to anion getter material 309 and thus in some embodiments the amount of anion getter material 309 within the first fluid 321 and/or second fluid 327 is less than the solubility limit, substantially the same as the solubility limit, or greater than the solubility limit. In one embodiment, a concentration of the solution (e.g., anion getter material 309 dissolved within first fluid 321 and/or second fluid 327) is 0.0001 weight percent. In other embodiments, the concentration of the solution is between 0.0001 weight percent and 0.01 weight percent. In yet other embodiments, the concentration of the solution is greater than 0.01 weight percent. In other embodiments, the solution may be a supersaturated solution (e.g., a greater amount of anion getter material 309 is dissolved within the solvent than the solubility limit), which may be obtained by dissolving the solute (e.g., anion getter material 309) in the solvent (e.g., first fluid 321 and/or second fluid 327) at an elevated temperature.

In some embodiments, anion getter material 309 may be stored in solid form in regions outside of central region 303 (e.g., within portions of first fluid 321, first window 311, and/or second window 313 within peripheral region 307) such that the solid form of anion getter material 309 does not interfere with light propagating through central region 303. In some embodiments, a mesh or other forms of containment may restrict the solid form of anion getter material 309 from moving to the central region 303, such that substantially only the dissolved form (e.g., liquid) of anion getter material 309 is within central region 303. In the same or other embodiments, anion getter material 309 may be dissolved, dispersed, or otherwise mixed within first window 311 and/or second window 313 during the fabrication process of first window 311 and/or second window 313 (e.g., anion getter material 309 is dissolved or otherwise mixed within a liquid compound that is cured to form first window 311 and/or second window 313). In some embodiments, anion getter material 309 is dispersed substantially uniformly throughout first window 311 and/or second window 313. In other embodiments, anion getter material 309 is not uniformly dispersed throughout first window 311 and/or second window 313. For example, in one embodiment, anion getter material 309 forms a concentration gradient (e.g., a larger amount of anion getter material 309 is concentrated within peripheral region 307 than central region 303). In some embodiments, nanoparticles (e.g., a diameter of anion getter material 309 in solid form is less than 100 nm) are dispersed heterogeneously or homogeneously throughout first window 311, second window 313, and/or first fluid 321. The nanoparticles may be a distinct size such that a diameter of the nanoparticles of anion getter material 309 are small enough that they do not substantially affect light propagating through central region 303. In general, particles may be smaller than the wavelength of light (e.g., within the optical electromagnetic spectrum) such that they do not cause scattering.

Figure 3B:
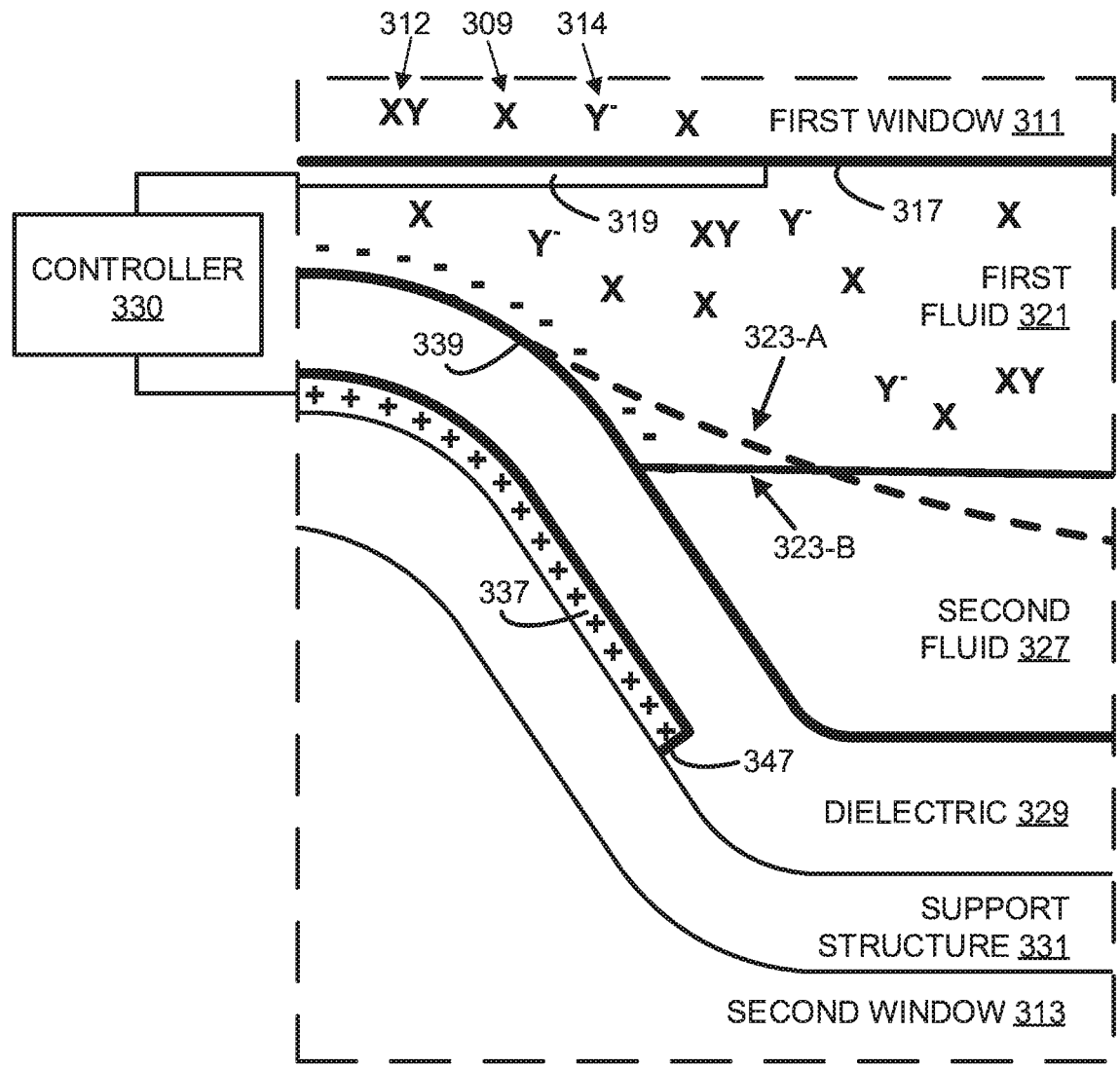
FIG. 3B illustrates a magnified view of a portion of the ophthalmic device of FIG. 3A, in accordance with an embodiment of the disclosure.

FIG. 3B illustrates a magnified view 336 of electrowetting cell 335 (illustrated in FIG. 3A) of an ophthalmic device with anion getter material 309 disposed within the ophthalmic device, in accordance with an embodiment of the disclosure. More specifically, FIG. 3B illustrates a shape and/or position of interface 323, which represents the boundary between first fluid 321 and second fluid 327, being adjusted, modified, or otherwise controlled by controller 330. Additionally, FIG. 3B illustrates a more detailed view of electrode 337 showing a barrier layer 347 coupled between electrode 335 and dielectric 329. Barrier layer 347 may be a metal oxide grown (e.g., via an anodization process during operation of electrowetting cell 335 and/or during fabrication of electrowetting cell 335) from a surface or interface of electrode 337. It is appreciated that while barrier layer 347 is illustrated as entirely coating the surface of electrode 337 that interfaces with dielectric 329, in some embodiments, barrier layer 347 may only exist proximate to defects of dielectric 329. In other words, during the anodization process, barrier layer 347 may be formed to compensate for the defects (e.g., caused by operation, physical manipulation of the device, or otherwise) to mitigate a short forming between electrode 337 and electrode 330. Further still, FIG. 3B illustrates anion getter materials 309 (represented by the "X" symbols) gettering (e.g., reacting, binding, interacting) anion contaminants 314 (represented by the "Y⁻" symbols) to form compounds (e.g., precipitates) 312 (represented by the "XY" symbols).

As discussed previously, electrowetting cell 335 provides optical power to an ophthalmic device via a lens defined by interface 323 between two immiscible fluids (e.g., first fluid 321 and second fluid 327). Since each of the two immiscible fluids have different refractive indexes, light propagating through the two immiscible fluids (e.g., through central region 303 illustrated in FIG. 3A) will be subject to imparted optical power, a degree of which is dependent, at least in part, on the difference in refractive indexes between first fluid 321 and second fluid 321, and a shape of the interface 323.

The shape of interface 323 may be adjusted or changed by electrowetting cell 335 via controller 330, which is analogous to controller 130 of FIG. 1 and/or controller 230 of FIG. 2B. Controller 330 leverages an electrowetting effect of the ophthalmic device (e.g., electrowetting cell 335) to adjust the wetting characteristics of the two immiscible fluids (e.g., first fluid 321 and/or second fluid 327) with respect to a surface proximate to dielectric 329 (e.g., the inner surface of dielectric 329 proximate to second repelling layer 339 and/or second repelling layer 339). The wetting characteristics are dependent on the relationship of the surface tension or energy between first fluid 321, second fluid 327, dielectric 329, and/or second repelling layer 339, which includes both chemical components and electrical components. The chemical components correspond to the intrinsic material properties of first fluid 321, second fluid 327, dielectric 329, and/or second repelling layer 339, while the electrical components corresponds to an applied external electrical force (e.g., an electric field generated by applying a potential difference between electrode 319 and 337).

Controller 330 is coupled to a power supply (e.g., battery 165 illustrated in FIG. 1) to apply a potential difference (or lack thereof) between electrode 319 and electrode 337 to modulate the wetting characteristics. Interface 323-A is representative of a default state of the electrowetting cell 335, in which a potential difference is not actively being applied between electrode 319 and electrode 337. Thus, in the default state, the electrical component of the surface tension is substantially insignificant relative to the chemical component.

In the illustrated embodiment of FIG. 3B, a shape of the interface 323 is changed (e.g., from interface 323-A to interface 323-B) by controller 330 transitioning from not actively applying a potential difference to actively applying a potential difference (e.g., a voltage) across and/or between electrode 319 and electrode 337. In some embodiments, the potential difference may be generated via direct or alternating current between electrode 319 and electrode 337. As illustrated, electrode 319 corresponds to a cathode and may be coupled through controller 330 to a reference or ground terminal of a power supply (e.g., battery 165 illustrated in FIG. 1). Conversely, electrode 337 corresponds to an anode and may be coupled through controller 330 to a positive terminal of a power supply (e.g., battery 165 illustrated in FIG. 1). In the illustrated embodiment, the potential difference generates an electric field between the electrodes 319 and 337, and in a manner similar to a capacitor, charge is built up proximate to opposing sides of dielectric 329, with negative charge proximate to the interface between first fluid 321 and dielectric 329, and positive charge proximate to the interface between electrode 337 and dielectric 329. The negative charge influences the wetting characteristics (e.g., the electrical component of the surface tension) between first fluid 321 and dielectric 329 making it more energetically favorable (relative to when the potential difference is not applied) for first fluid 321 to wet dielectric 329. Consequently, a shape of interface 323 shifts (e.g., from 323-A to 323-B) to transition to a more energetically favorable state (e.g., from a high energy state to a low energy state).

Advantageously, the electrowetting system for embodiments of ophthalmic devices described within the disclosure (e.g., ophthalmic device 105 of FIG. 1, ophthalmic device 205 of FIG. 2A, and/or electrowetting cell 335 of FIG. 3A) are self-healing systems. For example, in the embodiment illustrated in FIG. 3B, when there is a potential difference applied between electrode 337 and first fluid 321 (e.g., via electrode 319) a barrier layer 347 may be formed (e.g., via an anodization process). Barrier layer 347 may correspond to a metal oxide, which has a composition based on the underlying material composition of electrode 337, and is grown on the surface of electrode 337 proximate to dielectric 329. The anodization process compensates for damage to dielectric 329 by forming or growing a secondary dielectric (e.g., barrier layer 347) proximate to the damaged region of dielectric 329 (e.g., locally repaired), which collectively form a dielectric stack. Furthermore, if barrier layer 347 is damaged or is otherwise below some threshold thickness, the anodization process will continue to grow barrier layer 347 until the threshold thickness is reached. In other words, the anodization process may repair local damage to the dielectric stack (e.g., the combined dielectric stack of barrier layer 347 and dielectric 329) in the event that dielectric 329 and/or barrier layer 347 has been damaged (e.g., due to folding the ophthalmic device for insertion into the eye, dielectric breakdown during operation, and the like). Moreover, by repairing the dielectric stack, electrolysis of the first fluid 321 is reduced and/or prevented.

The anodization process may correspond to an electrochemical reaction between mobile metal cations (e.g., from electrode 337) and anions within first fluid 321 (e.g., $O^{2-}$ and/or $OH^-$ in embodiments where first fluid 321 is an aqueous solution) when the potential difference is applied between electrode 337 and first fluid 321 (e.g., via electrode 319). The metal cations from electrode 337 and anions from first fluid 321 are driven towards the metal/dielectric interface by the electric field resultant of the applied potential difference between electrode 337 and electrode 319, react accordingly, and form an anodic metal oxide (e.g., $Al_2O_3$, $AlO_x$, or other aluminum oxide variant in embodiments where electrode 337 comprises aluminum and the first fluid 321 is an aqueous solution). Thus is some embodiments, barrier layer 347 may correspond to local oxide growth on electrode 337 proximate to regions where dielectric 329 has been damaged (e.g., via dielectric breakdown). In the same or other embodiments, barrier layer 347 may not be limited to local oxide growth, but rather may coat the interface between electrode 337 and dielectric 329 having a thickness based on the magnitude of the potential difference applied between electrode 337 and electrode 319, the material composition of electrode 337, and duration of the anodization process.

However, anion contaminants may inhibit the anodization process from forming barrier layer 347 and thus reduce the effectiveness of the self-healing system. In fact, depending on the prevalence of the anion contaminants, the system may not self-heal at all. Furthermore, these anion contaminants may also corrode electrode 337 and/or barrier layer 347 (or other intrinsic metal oxide proximate to electrode 337), which could reduce the overall lifetime of the ophthalmic device. The anion contaminants may correspond to halide ions (e.g., chloride and/or fluoride ions). For example, in embodiments where the ophthalmic device (e.g., ophthalmic device 205 of FIG. 2A and/or electrowetting cell 335 of FIG. 3A) is implanted within the capsular bag of the eye, the ophthalmic device may be exposed to chloride ions that could, over time, diffuse into the device. Concentrations as low as 1 part per million of chloride ions may be detrimental to the anodization process, which is significantly lower than the expected concentration of chloride ions within the fluid around the capsular bag at around 2000 parts per million. The lens window (e.g., first window 311 and/or second window 313) is adapted to prevent ions from diffusing into the lens liquid (e.g., first fluid 321), but over a lifetime of twenty years, even a low diffusion coefficient could lead to unacceptably high levels of chloride within the lens liquid. Additionally, other inhibitors of the anodization process may also leech or diffuse into the lens liquid. For example, in some embodiments materials such as Parylene-C and/or Parylene-AF4 may be utilized which contain chlorine or fluorine atoms that over time could be released into the lens liquid. The anion contaminants may include other elements that may diffuse into barrier layer 347 and cause porosity (e.g., inhibit the anodization process) such as phosphates, sulfates, and selenates.

FIG. 3B illustrates a simplified diagram illustrating anion getter material 309 gettering anion contaminants 314 via a precipitation reaction, for example. As illustrated, anion getter material 309 is dissolved (e.g., soluble) within first fluid 321 and is adapted to getter anion contaminants 314 via a precipitation reaction between anion getter material 309 and anion contaminant 314 for forming a substantially insoluble (within the two immiscible fluids, such as first fluid 321 and second fluid 327) compound 312 (e.g., a precipitate) within the first fluid 321. In one embodiment, anion getter material 309 is a water-soluble salt such as silver nitrate, silver acetate, and/or silver salicylate that is dissolved within first fluid 321. The water-soluble salt reacts with the anion contaminant chloride (for example) and forms silver chloride via a precipitation reaction. Silver chloride has a low solubility (e.g., 0.2 ppm) within an aqueous solution (e.g., first fluid 321) and is small enough that it would not substantially inhibit optical clarity of the device. Silver chloride is also light sensitive, meaning that over time it will decompose under light, forming miniscule amounts of silver and chlorine gas, which in the case of chloride may diffuse out of the lens.

Similarly, other anion contaminants 314, such as fluoride, may also be gettered via a precipitation reaction between anion contaminant 314 and anion getter material 309. For example, in one embodiment, the anion getter material corresponds to water soluble calcium acetate that getters fluoride anions via a precipitation reaction to form insoluble (within either or both of the two immiscible fluids) calcium fluoride. Anion contaminants 314 such as phosphates, sulfates, and selenates known to interfere with the anodization process may also be gettered via a precipitation reaction via soluble (e.g., within first fluid 321) salts that contain anions that do not diffuse into, but may diffuse out of barrier layer 347. Examples of anion getter materials 309 comprising salts that may be used to getter anion contaminants 314 include antimonite, chromate, borate, molybdate, citrate, and tartrate.

In the same or other embodiments, anion getter material 309 may comprise of molecules structured to specifically target (e.g., chelate) a particular anion contaminant (e.g., chloride). More specifically, in one embodiment, anion getter material 309 may be an anion chelator that is structure so that the anion contaminant 314 fits within a gap at the center of the anion getter material 309 molecule and is held in place via multiple binding sites. An example of an anion getter material 309 that is an anion chelator is 1,2,3-triazoles which are able to getter chloride.

In other embodiments, anion getter material 309 may be a natural or synthetically derived mineral, such as hydrotalcite, to getter anion contaminants (e.g., chloride). In one embodiment, hydrotalcite may be partially dissolved within first fluid 321 or used in solid (e.g., undissolved) form when embedded in the lens (e.g., first window 311) in contact with first fluid 321. In solid form, hydrotalcite may be positioned outside of the optical area (e.g., within peripheral region 307 illustrated in FIG. 3A) such that it does not reduce optical quality of the ophthalmic device. Another example of a chloride anion getter is tricalcium aluminate, which would be used in solid (undissolved form) and/or as nanoparticles within first fluid 321. In one embodiment, anion getter material 309 could be insoluble, but have a diameter less than the wavelength of visible light (e.g., nanoparticles) such that they do not substantially interfere with the optical quality of the ophthalmic device.

It is appreciated that anion getter material 309 is not limited to being comprised of a single material targeting a single type of anion contaminant. Rather, anion getter material 309 may include one or more different materials to target one or more different types of anion contaminants. In one embodiment, the anion getter material 309 includes at least one of silver nitrate, silver acetate, silver salicylate, hydrotalcite, tricalcium aluminate, or triazoles. In the same or other embodiments, anion getter material 309 is adapted to getter anion contaminants including chloride ions and fluoride ions. Thus, anion getter material 309 may include a first anion getter (e.g., silver nitrate, silver acetate, silver salicylate, hydrotalcite, tricalcium aluminate, or triazoles) to getter chloride ions and a second anion getter material (e.g., calcium acetate) to getter fluoride ions. Moreover, is it appreciated that any of the examples of anion getter materials targeting one or more types of anion contaminants via varying mechanisms of gettering may be utilized individually or in combination, in accordance with embodiments of the disclosure.

Figure 4A:
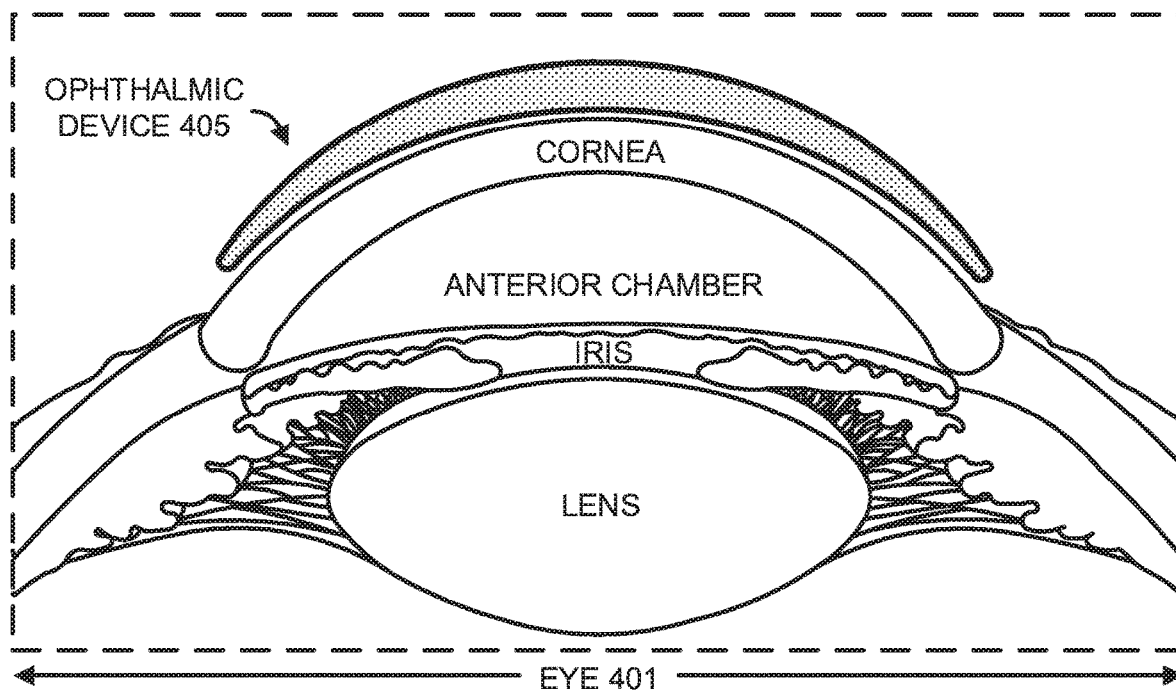
FIG. 4A illustrates a side view of an ophthalmic device mounted on an eye, in accordance with an embodiment of the disclosure.
Figure 4B:
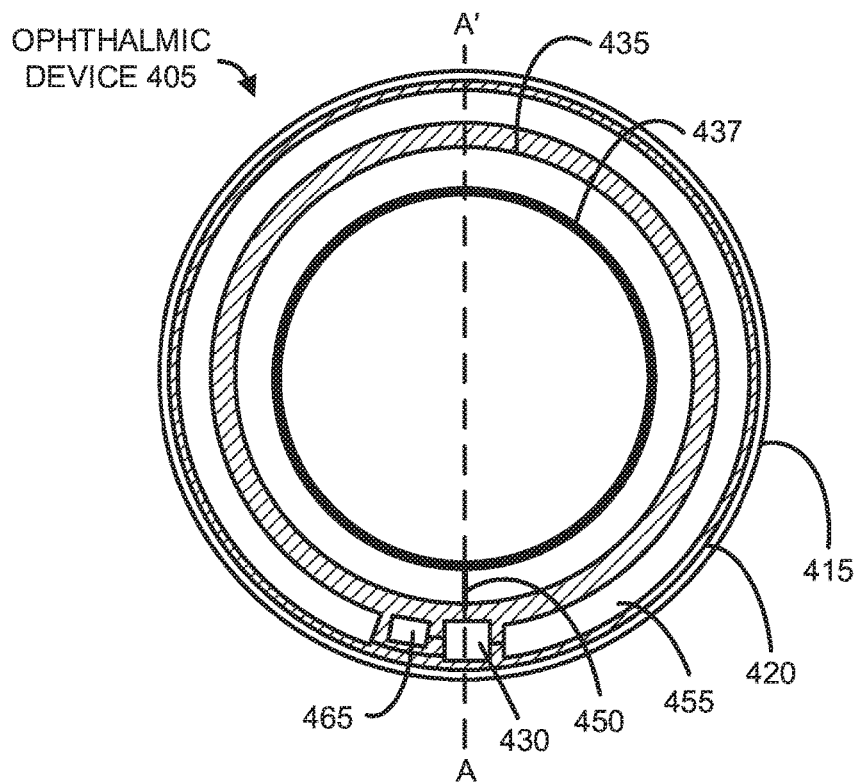
FIG. 4B illustrates a top view of an ophthalmic device, in accordance with an embodiment of the disclosure.
Figure 4C:
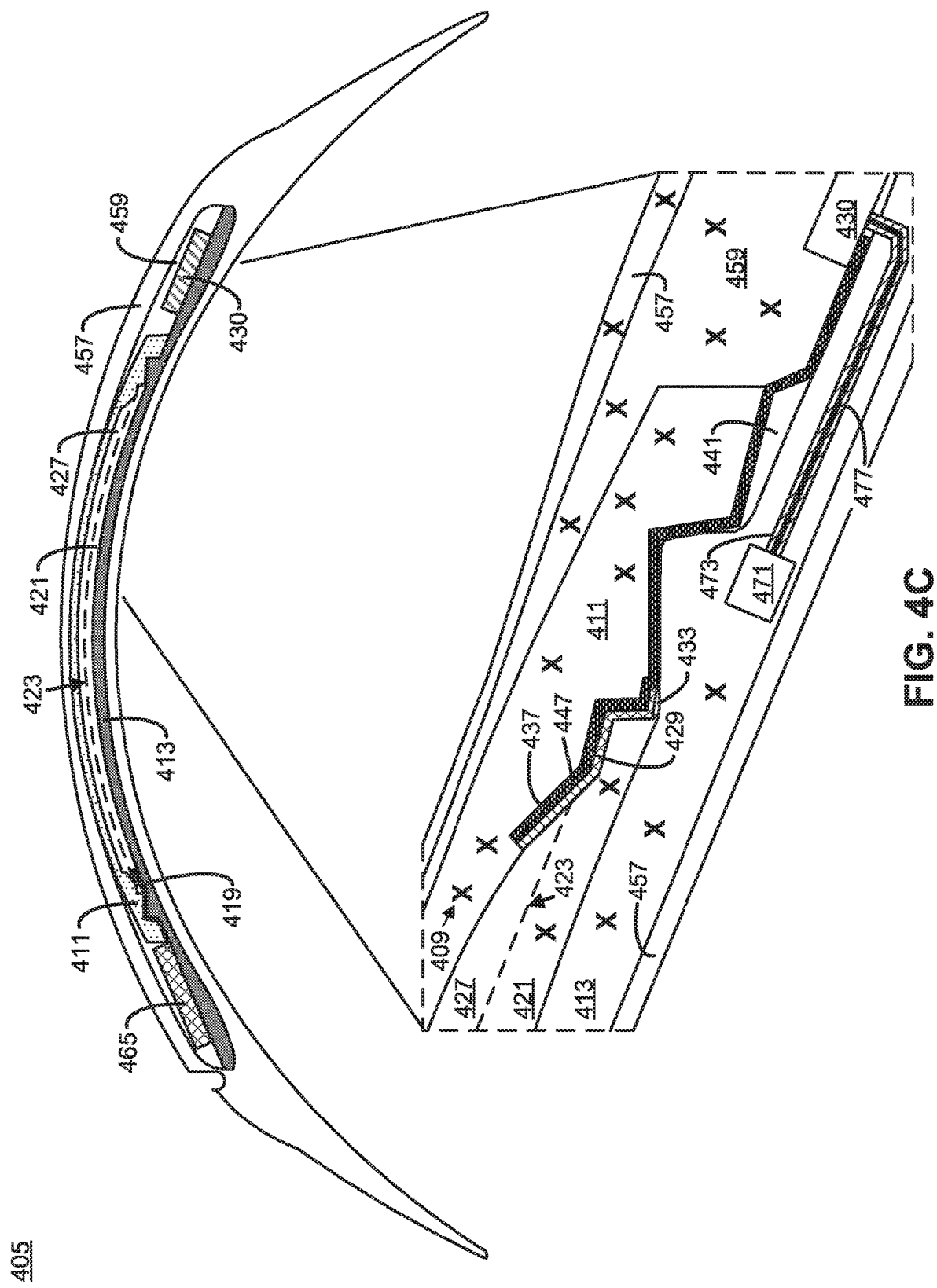
FIG. 4C illustrates a cross-sectional view of an ophthalmic device with an anion getter material disposed within the ophthalmic device, in accordance with an embodiment of the disclosure.

FIGS. 4A-4C respectively illustrate a side view, a top view, and a cross-sectional view of ophthalmic device 405, in accordance with an embodiment of the disclosure. Ophthalmic device 405 includes anion getter material 409, first window 411, second window 413, enclosure 415, substrate 420, first fluid 421, second fluid 427, interface 423, dielectric 429, controller 330, electrowetting cell 435, electrode 419, electrode 437, barrier layer 447, first sealant 433, second sealant 441, interconnect 450, antenna 455, and battery 465, which may be analogous to their identically named components included in ophthalmic device 105 illustrated in FIG. 1, ophthalmic device 205 illustrated in FIG. 2B, and/or electrowetting cell 335 illustrated in FIG. 3A. In other words, ophthalmic device 405 is one possible implementation of ophthalmic device 105, ophthalmic device 205, and/or electrowetting cell 335, and may include the same or similar features, structures, characteristics, or combination thereof in accordance with embodiments of the present disclosure.

As illustrated in FIG. 4A, ophthalmic device 405 is an eye-mountable device (e.g., contact lens) configured to be mounted on eye 401. More specifically, the illustrated embodiment shows ophthalmic device 405 having a concave surface configured to adhere ("mount") to a moistened corneal surface (e.g., by capillary forces with a tear film coating the corneal surface). Additionally or alternatively, ophthalmic device 405 may be adhered by a vacuum force between the corneal surface and the concave surface of the ophthalmic device.

In the illustrated embodiment of FIG. 4B, ophthalmic device 405 includes substrate 420, controller 430, electrowetting cell 435, electrode 437, interconnect 450, antenna 455, and battery 465 disposed within enclosure 410. Electrowetting cell 435 is centrally located within enclosure 415 and is coupled to controller 430 via interconnect 450 to provide accommodation to the user. More specifically, electrowetting cell 435 provides optical power that is adjustable based, at least in part, on an applied potential difference (e.g., voltage) between electrode 437 and a second electrode (e.g., electrode 419 illustrated in FIG. 4C). In the illustrated embodiment, electrode 437 is a conical electrode that extends around electrowetting cell 435. In other words, electrode 437 may form a loop, circle, oval, or otherwise define a boundary within electrowetting cell 435. The inner region formed by electrode 437 (e.g., the area encircled or enclosed by electrode 437) may correspond to a central region of ophthalmic device 405, while the outer region (e.g., the area outside of the central region) may correspond to a peripheral region of ophthalmic device 405.

FIG. 4C illustrates a cross-sectional view of an ophthalmic device 405 with an anion getter material 409 disposed within ophthalmic device 405, in accordance with an embodiment of the disclosure. Ophthalmic device 405 includes similar features to ophthalmic device 205 illustrated in FIG. 2A and electrowetting cell 335 illustrated in FIG. 3A and FIG. 3B and includes features and functions similar to the described embodiments of the present disclosure. However, ophthalmic device 405 includes some features not described in previous embodiments of the present disclosure, but that may also be included in the various embodiments (e.g., ophthalmic device 105 illustrated in FIG. 1, ophthalmic device 205 illustrated in FIG. 2A, and/or electrowetting cell 335).

In the illustrated embodiment, overmold 457 and encasement 459 may collectively correspond to an enclosure (e.g., enclosure 115 illustrated in FIG. 1, enclosure 215 illustrated in FIG. 2B, and/or enclosure 415 illustrated in FIG. 4A). Overmold 457 may comprise an optically transparent flexible material that is gas permeable to oxygen such as a silicone hydrogel or polyHEMA. Encasement 459 may comprise a transparent material (e.g., cross-linked silicone, epoxy, or otherwise) that encases controller 430, first window 411, battery 465 with second window 413. In some embodiments, encasement does not fully extend around first window 411, but rather seals controller 430 and/or battery 465 to second window 413. First window 411 may alternatively be referred to as an anterior element, while second window 413 may alternatively be referred to as a posterior element, each having alternative names that are indicative of their respective positions when ophthalmic device 405 is mounted on an eye. In the illustrated embodiment, second window 413 also functionally serves as a substrate (e.g., substrate 120 of FIG. 1, substrate 220 of FIG. 2B, and substrate 420 of FIG. 4A) for mounting the various components of ophthalmic device 405 (e.g., controller 430, battery 465, and the like). In some embodiments, the various components of ophthalmic device 405 may have a degree of oxygen permeability to allow for increased wearer comfort.

Ophthalmic device 405 includes an electrowetting system to provide accommodation to an eye of the user in a similar manner as described in regards to electrowetting cell 335 illustrated in FIG. 3A and FIG. 3B. Thus, a shape of interface 423 is controlled (e.g., via controller 430) to adjust optical power provided by a lens defined by the interface 423 between first fluid 421 and second fluid 427. The electrowetting system is similarly a self-healing system that forms barrier layer 447 during an anodization process. Anion getter material 409 getters anion contaminants (not illustrated) that may inhibit the anodization process as described in the various embodiments of the disclosure, and anion getter material 409 may be included in the various components of ophthalmic device 405 (e.g., overmold 457, encasement 459, first window 411, first fluid 421, and/or second window 413). In some embodiments, dielectric 429 is a hydrophobic dielectric (e.g., a fluoropolymer based dielectric such as Parylene AF-4). First and second sealants 433 and 441 respectively seal (e.g., prevent leaking) first fluid 421 and second fluid 427 between first window 411 and second window 413 to form an electrowetting cell.

As illustrated in FIG. 4C, controller 430 is coupled via a conductive trace 477 to a component 471 (e.g., an electrical component in an ophthalmic system, such as a sensor included in sensor system 140 of FIG. 1, battery 165 of FIG. 1, and the like). The conductive trace is embedded in insulating material 473 disposed within the enclosure (e.g., within any of the components enclosed by overmold 457 and/or within overmold 457). In one embodiment the insulating material is silicone and the conductive trace is a valve metal.

Figure 4D:
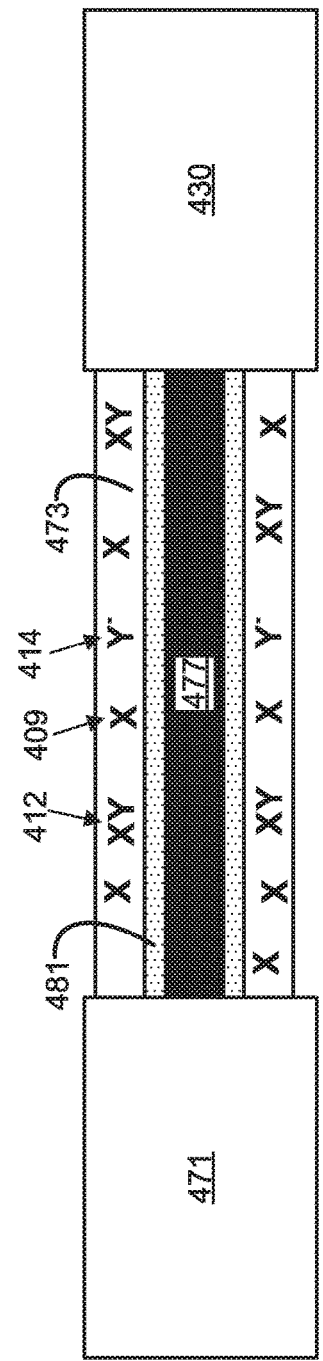
FIG. 4D illustrates a magnified view of a portion of the ophthalmic device of FIG. 4A, in accordance with an embodiment of the disclosure.

FIG. 4D illustrates a magnified view 405-D of a portion of the ophthalmic device 405 of FIG. 4C, in accordance with an embodiment of the disclosure. In the illustrated embodiment, component 471 is coupled to controller 430 via conductive trace 477. Conductive trace is a valve metal (e.g., at least one of aluminum, hafnium, niobium, tantalum, titanium, tungsten, vanadium, and/or zirconium) that has a thin (e.g., 2-3 nm thick) metal oxide 481 grown on the valve metal that inhibits corrosion of the valve metal. A composition of the metal oxide is based on the composition of the conductive trace (e.g., if the valve metal is aluminum, the metal oxide would be some variant of aluminum oxide such as $Al_2O_3$). The metal oxide is a self-healing oxide having similar features described in embodiments of the disclosure.

In one embodiment, controller 430 is configured to provide a supply voltage to electrical component 471 via conductive trace 477. In some embodiments, when the supply voltage is provided, damage or defects to metal oxide 481 are locally repaired (e.g., via an anodization process and/or through mobile ion rearrangement).

In the illustrated embodiment, anion getter materials 409 are represented by the "X" symbols, anion contaminants are represented by the "$Y^-$" symbols, and a precipitate or salt 412 is represented by the "XY" symbols. Anion contaminants 414 (e.g., halide ions) that may inhibit the self-healing effect of the conductive trace 477 and/or metal oxide 481 may be gettered by anion getter material 409, as described in embodiments of the disclosure. Anion getter material 409 may comprise of at least one of silver nitrate, silver acetate, silver salicylate, hydrotalcite, tricalcium aluminate, triazolophane, calcium acetate), and may getter anion contaminants 414 via various mechanisms as described in embodiments of the disclosure. In some embodiments, anion getter material 409 is adapted to getter anion contaminants 414 via a reaction between anion getter material 409 and anion contaminants 414 to form a salt 412 or other compound that is substantially immobile within insulating material 473. Anion getter material 409 may be dispersed heterogeneously or homogenously within insulating material 473. In one embodiment insulating material 473 is a silicone based material that has anion getter material 409 mixed within during fabrication of insulating material 473 (e.g., a liquid silicon resin is mixed with anion getter material 409 before the resin is cured to form insulating material 473).

The processes explained above are described in terms of computer software and hardware. The techniques described may constitute machine-executable instructions embodied within a tangible or non-transitory machine (e.g., computer) readable storage medium, that when executed by a machine (e.g., controller 130) will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An ophthalmic device, comprising:
an enclosure configured to mount on or in an eye;
two immiscible fluids disposed within the enclosure, wherein the two immiscible fluids include a first fluid and a second fluid;
an electrode separated from the two immiscible fluids by a dielectric, wherein the electrode is capable of forming a barrier layer during an anodization process when a voltage is applied across the electrode and the first fluid; and
an anion getter material disposed within the ophthalmic device, wherein the anion getter material is capable of gettering anion contaminants that inhibit the anodization process from forming the barrier layer.

2. The ophthalmic device of claim 1, wherein the barrier layer is formed during the anodization process to compensate for a defect within the dielectric.

3. The ophthalmic device of claim 1, wherein the anion getter material getters halide anions included in the anion contaminants.

4. The ophthalmic device of claim 3, wherein the anion getter material getters chloride ions included in the anion contaminants.

5. The ophthalmic device of claim 4, wherein the anion getter material includes at least one of silver nitrate, silver acetate, silver salicylate, hydrotalcite, tricalcium aluminate, or a triazole.

6. The ophthalmic device of claim 3, wherein the anion getter material getters fluoride ions included in the anion contaminants.

7. The ophthalmic device of claim 3, wherein the anion getter material getters chloride ions and fluoride ions included in the anion contaminants, and wherein the anion getter material includes a first anion getter to getter the chloride ions and a second anion getter to getter the fluoride ions.

8. The ophthalmic device of claim 7, wherein the first anion getter material includes at least one of silver nitrate, silver acetate, silver salicylate, hydrotalcite, tricalcium aluminate, or a triazole, and wherein the second getter material includes calcium acetate.

9. The ophthalmic device of claim 1, wherein the anion getter material is disposed within the first fluid included in the two immiscible fluids.

10. The ophthalmic device of claim 9, wherein the anion getter material is soluble within the first fluid, and wherein the anion getter material getters the anion contaminants via a precipitation reaction between the anion getter material dissolved within the first fluid and the anion contaminants to form a substantially insoluble compound within the first fluid.

11. The ophthalmic device of claim 1, wherein the enclosure includes a first optical window and a second optical window configured to encapsulate the two immiscible liquids, and wherein the anion getter material is disposed within at least one of the first fluid, the first optical window, or the second optical window.

12. The ophthalmic device of claim 11, wherein an interface defined by the two immiscible fluids forms a lens within a central region of the ophthalmic device, and wherein the anion getter material is disposed in a peripheral region outside of the central region.

13. The ophthalmic device of claim 12, wherein the anion getter material is disposed within the first fluid, and wherein the first fluid is saturated with the anion getter material such that a portion of the anion getter material is undissolved by the first fluid.

14. The ophthalmic device of claim 1, wherein the anion getter material is an anion chelator structured to chelate the anion contaminants.

15. The ophthalmic device of claim 1, wherein the anion getter material getters at least one of phosphate, sulfate, or selenate included in the anion contaminants, wherein the anion getter material includes a salt soluble within the first fluid, and wherein the salt includes at least one of antimonite, chromate, borate, molybdate, citrate, or tartrate.

16. The ophthalmic device of claim 1, wherein the electrode comprises a valve metal, and wherein the barrier layer is a metal oxide grown on a surface of the valve metal proximate to the dielectric during the anodization process, and wherein the barrier layer compensates for a defect within the dielectric proximate to the barrier layer.

17. The ophthalmic device of claim 16, wherein the valve metal comprises at least one of aluminum, hafnium, niobium, tantalum, titanium, tungsten, vanadium, or zirconium, wherein the metal oxide is based on a composition of the valve metal, and wherein the dielectric comprises at least one of Parylene-C, Parylene-N, Parylene-D, or Parylene-AF4.

18. An ophthalmic system, comprising:
an enclosure configured to mount on or in an eye;
an insulating material disposed within the enclosure, wherein the insulating material includes an anion getter material disposed within the insulating material; and
a conductive trace embedded within the insulating material, wherein the conductive trace includes a valve metal, and wherein the anion getter material is capable of gettering anion contaminants to inhibit the anion contaminants from diffusing through the insulating material.

19. The system of claim 18, further comprising:
a controller coupled to an electrical component via the conductive trace, wherein the controller is configured to provide a supply voltage to the electrical component via the conductive trace, and wherein the conductive trace includes a metal oxide layer grown on the valve metal that is locally repaired when the supply voltage is provided.

20. The system of claim 18, wherein the valve metal comprises at least one of aluminum, hafnium, niobium, tantalum, titanium, tungsten, vanadium, or zirconium, and wherein the metal oxide is based on a composition of the valve metal.

21. The system of claim 18, wherein the anion getter material getters halide anions included in the anion contaminants.

22. The system of claim 21, wherein the anion getter material getters the anion contaminants via a reaction between the anion getter material and the anion contaminants to form a salt.

23. The system of claim 21, wherein the anion getter material includes at least one of silver nitrate, silver acetate, silver salicylate, hydrotalcite, tricalcium aluminate, or calcium acetate.

* * * * *